United States Patent
Bruder et al.

(10) Patent No.: US 10,026,203 B2
(45) Date of Patent: Jul. 17, 2018

(54) METHOD FOR RECONSTRUCTION OF SPECTRAL RESULT IMAGE DATA

(71) Applicant: Siemens Healthcare GmbH, Erlangen (DE)

(72) Inventors: Herbert Bruder, Hoechstadt (DE); Karl Stierstorfer, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/703,015

(22) Filed: Sep. 13, 2017

(65) Prior Publication Data

US 2018/0075627 A1 Mar. 15, 2018

(30) Foreign Application Priority Data

Sep. 15, 2016 (DE) .................. 10 2016 217 639

(51) Int. Cl.
*G06K 9/00* (2006.01)
*G06T 11/00* (2006.01)
(Continued)

(52) U.S. Cl.
CPC ............ *G06T 11/003* (2013.01); *A61B 6/032* (2013.01); *A61B 6/4035* (2013.01); *A61B 6/54* (2013.01);
(Continued)

(58) Field of Classification Search
CPC ... G06T 11/006; G06T 11/003; G06T 7/0012; G06T 7/0081; G06T 2207/10081;
(Continued)

(56) References Cited

U.S. PATENT DOCUMENTS 4,506,327 A 3/1985 Tam
7,103,135 B2 * 9/2006 Koppe ................. G06T 11/005
378/15
(Continued)

OTHER PUBLICATIONS

Chen G., Li Y.,: "SMART-RECON: A statistical model based iterative image reconstruction method to eliminate limited-view artifacts and to mitigate the temporal-average artifacts in time-resolved CT", in: Med. Phys., vol. 42. Nr. 8, pp. 4698-4707.

(Continued)

*Primary Examiner* — Amir Alavi
(74) *Attorney, Agent, or Firm* — Harness, Dickey & Pierce, P.L.C.

(57) ABSTRACT

A method is for imaging of an examination region of an object to be examined with a computed tomography system. In an embodiment, the method includes recording of first and second projection measurement data with a common x-ray source-detector system, the first projection measurement data being recorded with a first x-ray spectrum in a first angular sector and the second projection measurement data being recorded with a second x-ray spectrum in a second angular sector; Creation of first and second start image data from the first and second projection measurement data via a first reconstruction method; and coupled iterative reconstruction of first result image data on the basis of the first start image data and of second result image data on the basis of the second start image data, the first result image data and the second result image data each featuring a complete image of the examination region.

28 Claims, 4 Drawing Sheets

(51) Int. Cl.
*A61B 6/03* (2006.01)
*A61B 6/00* (2006.01)

(52) U.S. Cl.
CPC ........... *A61B 6/482* (2013.01); *G06T 2210/41* (2013.01); *G06T 2211/436* (2013.01)

(58) Field of Classification Search
CPC ........... A61B 6/4291; A61B 6/40; A61B 6/00; A61B 6/0306
See application file for complete search history.

(56) References Cited

U.S. PATENT DOCUMENTS

| | | | |
|---|---|---|---|
| 9,626,778 B2* | 4/2017 | Stayman | G06T 11/006 |
| 9,652,831 B2* | 5/2017 | Mahnken | G06T 5/001 |
| 2006/0062443 A1* | 3/2006 | Basu | G06T 11/005 |
| | | | 382/131 |
| 2016/0256122 A1* | 9/2016 | Heid | A61B 6/4035 |
| 2016/0287205 A1* | 10/2016 | Zou | A61B 6/585 |
| 2016/0296183 A1* | 10/2016 | Flohr | A61B 6/032 |
| 2016/0302756 A1* | 10/2016 | Fan | G06T 5/002 |
| 2016/0317113 A1* | 11/2016 | Allmendinger | A61B 6/507 |

OTHER PUBLICATIONS

German Office Action Number: DE 2016P13415 dated Apr. 5, 2017.

* cited by examiner

METHOD FOR RECONSTRUCTION OF SPECTRAL RESULT IMAGE DATA

PRIORITY STATEMENT

The present application hereby claims priority under 35 U.S.C. § 119 to German patent application number DE 102016217639.0 filed Sep. 15, 2016, the entire contents of which are hereby incorporated herein by reference.

FIELD

At least one embodiment of the invention generally relates to a method and to an image reconstruction device, a computed tomography system, a computer program product and a computer-readable medium for reconstruction of spectral result image data.

BACKGROUND

Computed tomography is an imaging method, which is used above all for medical diagnostics and also for examination of materials. In computed tomography, to record spatially three-dimensional image data, a radiation source, for example an x-ray source, and also a detector facility interacting with said source, rotate around an object to be examined. During the rotational movement measurement data is recorded within an angular sector. The projection measurement data involves a plurality of projections, which contain information about the attenuation of the radiation by the examination object from different projection angles. A two-dimensional slice image or a three-dimensional volume image of the examination object is able to be computed from these projections. The projection measurement data is also referred to as raw data or the projection measurement data can already be pre-processed data, so that for example detector-related intensity differences in the attenuation are reduced. Image data can then be reconstructed from this projection measurement data, by way of what is known as filtered back projection for example, or via an iterative reconstruction method. If the examination object moves during the recording, unsharp areas and artifacts resulting from the movement can occur during the reconstruction of the image data.

Multifarious methods for scanning an examination object with a computed tomography system are known. Orbital scans, sequential orbital scans with advance or spiral scans are employed for example. Other types of scanning, which are not based on orbital movements, are also possible, thus scans with linear segments for example. Absorption data of the examination object is recorded from different recording angles with the aid of at least one x-ray source and at least one opposing detector apparatus and this absorption data or the projections collected in this way are computed into slice images through the examination object via corresponding recording methods.

For reconstruction of computed tomography images from the projection measurement data of a computed tomography system, what is known as a filtered back projection method (FBP) is used as the standard method nowadays. However, because of their approximative method of operation, there are problems with the classical FBP methods with so-called cone beam artifacts, spiral artifacts and limited-view artifacts. Furthermore, with classical FBP methods, the image sharpness is coupled to the image noise. The higher the sharpness achieved is, the higher is also the image noise and vice versa.

The FBP method belongs to the group of approximative reconstruction methods. The group of exact reconstruction methods, which is currently hardly used however, also exists. The iterative methods form a third group of reconstruction methods.

With iterative reconstruction methods at least some of the stated limitations of FBP can be overcome. With such an iterative reconstruction method there is first of all a reconstruction of start image data from the projection measurement data. A filtered back projection method can be used for this purpose for example. The iterative reconstruction method subsequently gradually creates improved image data. Synthetic projection data can be created from the start image data with a "projector", a projection operator that is designed to map the measurement system mathematically as well as possible for example. The difference from the measurement signals will then be projected back with the operator adjoint to the projector and in this way a residual image reconstructed, with which the initial image will be updated. The updated image data in its turn can be used, in a next iteration step, with the aid of the projection operator, to create new synthetic projection data, to once again form the difference from the measurement signals from this and compute a new residual image, with which the image data of the current iteration stage will again be improved etc. Such a method allows image data that has a relatively good image sharpness and still has a low level of image noise to be reconstructed. Examples of iterative reconstruction methods are the Algebraic Reconstruction Technique (ART), the Simultaneous Algebraic Reconstruction Technique (SART), the Iterated Filtered Back Projection (IFBP), or also statistical iterative image reconstruction techniques.

Counting direct-converting x-ray detectors or integrating indirect-converting x-ray detectors can be used in computed tomography. The x-ray radiation or the photons can be converted in direct-converting x-ray detectors by a suitable converter material into electrical pulses. The level of the electrical pulses is as a rule proportional to the energy of the absorbed x-ray photon. This enables spectral information to be extracted by comparing the level of the electrical pulse with a threshold value. The x-ray radiation of the photons can also be converted into light by a suitable converter material in indirect-converting x-ray detectors and via photodiodes into the electrical pulse. The level of the electrical pulse specifies an integral intensity of the detected x-ray radiation.

In dual-energy computed tomography (Dual Energy CT), dual-source computed tomography (Dual Source CT) as well as with the use of energy-resolving counting x-ray detectors, for example direct-converting x-ray detectors, material decompositions into two or three materials can be carried out on the basis of the measured datasets. In dual-energy computed tomography different spectra can be created for example by switching back and forth between different tube voltages or by the use of a filter partly embodied in the beam path. In dual-source computed tomography the two x-ray sources can be operated with different tube voltages. The inventors have recognized that it is difficult to create more than two spectral datasets with one single x-ray source.

A method for time-resolved computed tomography, which provides a new method for elimination of limited-view artifacts, is known from G. Chen, Y. Li, "Synchronized multiartefact reduction with tomographic reconstruction (SMART-RECON): A statistical model based iterative image reconstruction method to eliminate limited-view artifacts and to mitigate the temporal-average artifacts in time-resolved CT", Med. Phys. 42, 4698 (2015). In this method data recorded in an ultrashort time window, which corresponds to angular ranges of around 60°, is used.

SUMMARY

At least one embodiment of the invention specifies a method and also an image reconstruction device, a computed tomography system, a computer program product and a computer-readable medium, which make possible the reconstruction of a complete spectral image based on images recorded in a small angular sector.

At least one embodiment of the invention is directed to a method; at least one embodiment of the invention is directed to an image reconstruction device; at least one embodiment of the invention is directed to a computed tomography system; at least one embodiment of the invention is directed to a computer program product and at least one embodiment of the invention is directed to a computer-readable medium.

At least one embodiment of the invention relates to a method, for imaging an examination region of an object to be examined with a computed tomography system, comprising: recording, creating of first and second start image data, and coupled iterative reconstruction.

In the recording, first projection measurement data and second projection measurement different from the first projection measurement data are recorded with a common x-ray source-detector system, wherein the first projection measurement data is recorded with a first x-ray spectrum in a first angular sector of maximum 180° and the second projection measurement data with a second x-ray spectrum different from the first x-ray spectrum in a second angular sector of maximum 180° disjoint from the first angular sector.

In the creation, first start image data is created from the first projection measurement data and second start image data from the second projection measurement data via a first reconstruction method, in particular of a known reconstruction method, preferably by way of a filtered back projection. The first reconstruction method is different from the coupled iterative reconstruction. The first reconstruction method can for example comprise a filtered back projection or a known iterative reconstruction.

In the coupled iterative reconstruction, first result image data is reconstructed on the basis of the first start image data and second result image data on the basis of the second start image data, wherein the first result image data and the second result image data each feature a complete image of the examination region.

An embodiment of the invention further relates to an image reconstruction device for carrying out an embodiment of the inventive method. The image reconstruction device has an input interface for acquiring projection measurement data from an examination region of an object to be examined obtained via a computed tomography system with the aid of a recording, a reconstruction unit for reconstructing result image data on the basis of the acquired projection measurement data, and an image data interface for output of the reconstructed result image data. Advantageously, in an embodiment, all steps of an embodiment of the inventive method can be carried out in the image reconstruction device.

An embodiment of the invention further relates to a computed tomography system, which has a projection data recording unit, comprising an x-ray source and a detector apparatus for recording of projection measurement data of an examination region of an object to be examined, a control device for activating the projection data recording unit and an image reconstruction device. Advantageously, in an embodiment, the computed tomography system is configured for carrying out an embodiment of the method.

An embodiment of the invention further relates to a computer program product with a computer program, which is able to be loaded directly into a memory device of a computed tomography system, with program sections for carrying out all steps of an embodiment of the inventive method when the computer program is executed in the control device of the computed tomography system. Advantageously, in an embodiment, the computer program product can be used so that a computed tomography system can carry out an embodiment of the inventive method.

An embodiment of the invention further relates to a computer-readable medium, on which program sections able to be read in and executed by a computing unit are stored, in order to execute all steps of an embodiment of the inventive method when the program sections are executed by the processing unit. Advantageously, in an embodiment, the computer-readable medium can be used so that a computed tomography system can carry out an embodiment of the inventive method.

BRIEF DESCRIPTION OF THE DRAWINGS

Example embodiments of the invention are explained in greater detail below with reference to drawings. In the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method, for imaging an examination region of an object to be examined with a computed tomography system, comprising: recording, creating of first and second start image data, and coupled iterative reconstruction.

In the recording, first projection measurement data and second projection measurement different from the first projection measurement data are recorded with a common x-ray source-detector system, wherein the first projection measurement data is recorded with a first x-ray spectrum in a first angular sector of maximum 180° and the second projection measurement data with a second x-ray spectrum different from the first x-ray spectrum in a second angular sector of maximum 180° disjoint from the first angular sector.

In the creation, first start image data is created from the first projection measurement data and second start image data from the second projection measurement data via a first reconstruction method, in particular of a known reconstruction method, preferably by way of a filtered back projection. The first reconstruction method is different from the coupled iterative reconstruction. The first reconstruction method can for example comprise a filtered back projection or a known iterative reconstruction.

In the coupled iterative reconstruction, first result image data is reconstructed on the basis of the first start image data and second result image data on the basis of the second start image data, wherein the first result image data and the second result image data each feature a complete image of the examination region.

The inventors propose, in an embodiment, that the recording of the projection measurement data be divided up such that the projection measurement data is recorded in disjoint angular sectors with different x-ray spectra. The spectral separation can be brought about by different voltages, different diaphragms or filters in the beam path, for example arranged at a short distance from the x-ray source, or by a combination of the two options.

The projection measurement data can be recorded in a single scan with a common x-ray source-detector system, i.e. for example while the system is advancing in a single direction and during an orbit. The projection measurement data can in particular comprise pre-processed raw data, which for example already takes account of corrections of detector-related or geometrical differences between the registered intensities. The first projection measurement data can be pre-processed differently from the second projection measurement data.

In spiral scanning the length of the data area of a slice or of a slice volume is dependent on the speed of advance of the table relative to the x-ray source-detector system. For the maximum advance only around half an orbit with projection measurement data per slice can be available for example. Consequently for example three disjoint angular sectors can only cover around 60° or 80°, or in a more general embodiment can cover less than 180°.

In the separate reconstruction of the projection measurement data of the disjoint angular sectors, for example via filtered back projection, so-called limited-view artifacts occur, since during the recording of a specific point in the object during the recording of the, for example first, projection measurement data of the, for example first, angular sector, not all planes intersect with this specific point of the recording trajectory at least once. The start image data is not complete images, since the start image data will be reconstructed from the projection image data with maximum 180° and the projection image data used for reconstruction is not sufficient for the minimum requirement of the sum of 180° and the fan angle of the incident x-ray beam cone or fan for, in particular exact, reconstruction of a complete image by way of a conventional reconstruction method. In particular with an angular sector comprising less than 180° minus the fan angle there are likely to be limited-view artifacts, so that the reconstruction of incomplete sub-images is also made more difficult.

The first, second and any further start image data can be entered as vectors $\vec{X}^1, \ldots, \vec{X}^N$ in a spatial-spectral image matrix X, wherein the start image data for the different x-ray spectra is entered into the columns of the image matrix.

$$X = (\vec{X^1}, \ldots, \vec{X^N}) = \begin{pmatrix} X_1^1 & \ldots & X_1^N \\ \vdots & \ddots & \vdots \\ X_M^1 & \ldots & X_M^N \end{pmatrix} \quad (1)$$

The image matrix can be an M×N matrix, wherein the image vectors each have M entries and the number of the x-ray spectra can amount to N for example. The vectors of the start image data, recorded with different x-ray spectra, can be arranged in the image matrix, wherein the entries of the image voxels are arranged in one dimension and the spectral information is arranged in the other dimension. The matrix can also be written as a column vector $\vec{X}$ with MN rows. The forward projection can be as follows:

$$\vec{Y} = A\vec{X}, \quad (2)$$

wherein A is the system matrix.

The result image data can be iteratively reconstructed by minimizing a suitable cost function with suitable regularization. The regularization term can be defined as follows:

$$\psi(X) = \|X\|_* = \|U\Sigma V^{tr}\| = \Sigma_r \sigma_r. \quad (3)$$

In this case $X = U\Sigma V^{tr}$ can be the singular value decomposition of the matrix X. U and V can be two orthogonal matrixes. $\Sigma = \text{diag}(\sigma_r)$ is a diagonal matrix. The values $\sigma_r$ (r=1,2, . . . ) are known as singular values of the matrix X. During the regularization in this case, the nuclear norm of the image matrix can in particular be forced to be minimized. The nuclear norm can be defined in this case as the sum of the singular values of the image matrix.

The iterative reconstruction can be formulated as follows as a convex optimization problem:

$$\tilde{X} = \arg\min_X [½(\vec{Y} - A\vec{X})^{tr} D(\vec{Y} - A\vec{X}) + \lambda \|X\|_*]. \quad (4)$$

The parameter λ can be introduced in order to undertake a weighting between the fidelity of the data and the regularization strength. The diagonal noise matrix D can have an inverse of the noise variance of logarithmized data, in particular projection measurement data, as its diagonal elements. The convex optimization problem can be solved for example by an alternating updating method, wherein the original optimization problem is divided into two sub-problems:

$$\vec{X}^{(k)} = \arg\min_X [½(\vec{Y} - A\vec{X})^{tr} D(\vec{Y} - A\vec{X})] \quad (5)$$

and $$X^{(k+1)} = \arg\min_X \|X - X^{(k)}\|_F^2 + \lambda \psi(X), \quad (6)$$

wherein $\|X\|_F^2 := \Sigma_{ij} X_{ij}^2$ is the Frobenius norm of the matrix X.

To compute $\vec{X}^{(k)}$, a noise-weighted mandatory data fidelity condition is applied to the reconstruction of each spectral dataset, in order to obtain a provisional intermediate image vector $\vec{X}^{(k)}$ with MN rows. This intermediate image vector is converted back into the M×N matrix $X^{(k)}$. For computation of $X^{(k+1)}$ the nuclear norm $\|X\|_*$ can be used as a regularizer, in order to define a modified denoising problem. This enables limited-view artifacts and image noise to be advantageously reduced.

The result image data can only be reconstructed from incomplete start image data, which is affected by limited-view artifacts. Therefore the rank of the image matrix X can preferably differ from the ideal value 1, the rank of the image matrix can in particular be reduced, and the rank of the nuclear norm of the matrix can be increased. Advantageously the limited-view artifacts can be reduced by the enforcing of a minimal nuclear norm. The parameter λ can be used to control the weighting of the equality of the spectral images and the strength of the limited-view artifacts in the reconstructed result image data.

To solve the two sub-problems a gradient descent method for iterative solution can be used. To solve the quadratic problem for computation of $\vec{X}^{(k)}$ the following updating sequence can be used:

$$\vec{X}^{(k)} = \vec{X}^{(k-1)} + \delta A^{tr} D[\vec{X} - A\vec{X}^{(k-1)}]. \quad (7)$$

After the kth iteration of the intermediate image vector $\vec{X}^{(k)}$ this is converted back into the spatial-spectral image matrix $X^{(k)}$. The parameter δ can specify a step size for updating. The parameter δ can amount to 0.25 for example.

The coupled iterative reconstruction, by simultaneously taking account of the first, second and any further start image data, can advantageously create complete result image data. The minimization condition advantageously enables the limited-view artifacts to be reduced. The coupled iterative reconstruction makes possible, in particular in each case, a complete first image on the basis of the first projection measurement data of the first x-ray spectrum. The same applies to the second and to any further projection measurement data. Advantageously the time resolution can be increased. The spectral result image data can be output as column vectors of the image matrix. The first result image data can be presented such that a first complete image is shown. The same applies to the second and to any further result image data.

The first, second and any further angular sector can comprise an angular range of far less than 180°. The first, second and any further angular sector can comprise an angular range of 60° to 180°, preferably of 70° to 140° and especially preferably of 80° to 120°. The angular sectors can comprise different angular ranges. Advantageously a number of complete spectral result images can be reconstructed from the recordings in the angular sectors. Advantageously information can be used from the similarity between the start image data in the coupled iterative reconstruction, so that the limited-view artifacts can be reduced or prevented.

For example an angular sector can comprise a larger angular area, so that a set of result image data advantageously has better image characteristics. Advantageously in this case the image matrix can additionally have start image data recorded in a larger angular sector, for example of at least the sum of 180° and the fan angle, so that this spectral image per se is not adversely affected by limited-view artifacts and in addition at least two further spectral images, for example based on projection measurement data from an angular sector of 360° minus 180° minus fan angle, can be provided.

Advantageously embodiments of the inventive method can also be used for dual-source computed tomographs, wherein each x-ray source-detector system carries out embodiments of the inventive method and the time resolution for the spectral images, for example in heart imaging, can be doubled by the use of two x-ray source-detector systems.

Advantageously embodiments of the inventive method can be carried out with an indirect-converting x-ray detector, wherein any material decomposition into more than two basic materials is made possible. Advantageously embodiments of the inventive method can be carried out with a direct-converting x-ray detector, wherein for example an improved spectral separation or the decomposition into a further basic material is made possible. The first and second result image data as well as any further result image data can advantageously be shown in a common mixed image by pixel-by-pixel weighting as a linear combination.

In accordance with an embodiment of the invention, complete start image data of a complete start image from a common reconstruction based on a number of projection measurement data of a record is taken into account in the coupled iterative reconstruction.

The complete start image data can be entered as vectors $\vec{X^0}$ in a column of the image matrix.

$$X_p = (\vec{X^0} \mid X) = (\vec{X^0}, \vec{X^1}, \ldots, \vec{X^N}) = \begin{pmatrix} X_1^0 & X_1^1 & \ldots & X_1^N \\ \vdots & \vdots & \ddots & \vdots \\ X_M^0 & X_M^1 & \ldots & X_M^N \end{pmatrix} \quad (8)$$

The image matrix can accordingly be an M×(N+1) matrix, all further method steps can be carried out similarly to the use of the M×N matrix. The complete start image data comprises projection measurement data from more than 180°, in particular from at least the sum of 180° and the fan angle. For example the complete start image data can be reconstructed jointly from the first, second and any further projection measurement data. The complete start image data can be reconstructed for example via filtered back projection. The complete start image data can deliver a complete image of the examination region, however it can have a non-uniform intensity distribution through the simultaneous taking into account of the projection measurement data of different x-ray spectra. The taking into account of complete start image data in the image matrix advantageously improves the reduction of limited-view artifacts.

In accordance with an embodiment of the invention, third projection measurement data with a third x-ray spectrum different from the first x-ray spectrum and from the second x-ray spectrum is recorded in addition in a third angular sector of maximum 180°, disjoint from the first angular sector and from the second angular sector. The third projection measurement data can be referred to as further projection measurement data.

The expansion to three different x-ray spectra can make any material decomposition into three basic materials possible. Advantageously any material decomposition into the basic materials can be achieved with a single-source computed tomograph, in particular even with high speeds of advance. The use of three different x-ray spectra can therefore be especially advantageous.

In accordance with an embodiment of the invention, the coupled iterative reconstruction comprises a minimization with a regularization.

The minimization can be a minimization of a pre-determined cost function. The coupled iterative reconstruction comprises a minimization of a cost function with a regularization with so-called sparsity boundary conditions. The coupled iterative reconstruction can be a gradient descent method, for example based on the method of least square. The coupled iterative reconstruction can comprise a penalty term for regularization, wherein the image matrix assumes a low rank and the regularization assumes a high rank. In the regularization the nuclear norm of the image matrix can be minimized, wherein the sum of the singular values is minimized via singular value decomposition. The image information can be taken in particular from the singular values of the image matrix, which will be used within the framework of the regularization as nuclear norm of the image matrix. The regularization of the image matrix comprises so-called sparsity boundary conditions. The coupled iterative reconstruction can further comprise a data weighting matrix for maintaining contrast and determining the noise behavior. The data weighting matrix enables the distance of the forward projection from the start image data to be minimized. Advantageously the result image data can feature a complete image in each case.

In accordance with an embodiment of the invention the inventive method also has the step of a material decomposition on the basis of the result image data. The first, second and any third result image data can be represented as a pixel-by-pixel linear combination and a material decomposition into two or three basic materials can be achieved. The material decomposition makes it possible to present material images based on one basic material in each case. For example gadolinium, iodine, calcium or water can be used as the basic material. Advantageously one material image can be shown in each case for water, calcium and contrast media, for example gadolinium or iodine. Advantageously a diagnosis can be simplified on the basis of the different material images or material images mixed with one another.

In accordance with an embodiment of the invention the average photon energy or the maximum photon energy of the different x-ray spectra differs by at least 10 keV. The different average photon energy or the maximum photon energy enables a separation or an overlap that is as small as possible between the different x-ray spectra to be achieved. Preferably the average photon energy can differ by at least 10 keV, in order to achieve especially advantageously different x-ray spectra.

In accordance with an embodiment of the invention a switchover between the different x-ray spectra comprises a use of a filter in the beam path of the x-ray source or a change of a tube voltage of the x-ray source.

A filter or a diaphragm can be used for example to switch between different x-ray spectra. For example a tin filter can be used. The different spectra can be designed such that the overlap of the intensities of the individual energies in the spectra is advantageously as small as possible, in order to reduce a linear dependency between the projection measurement data. With the use of changed tube voltages, a tube voltage of 70 kV can be used for example for the first x-ray spectrum, a tube voltage of 120 kV for the second x-ray spectrum and a tube voltage of 150 kV for the third x-ray spectrum.

An embodiment of the invention further relates to an image reconstruction device for carrying out an embodiment of the inventive method. The image reconstruction device has an input interface for acquiring projection measurement data from an examination region of an object to be examined obtained via a computed tomography system with the aid of a recording, a reconstruction unit for reconstructing result image data on the basis of the acquired projection measurement data, and an image data interface for output of the reconstructed result image data. Advantageously, in an embodiment, all steps of an embodiment of the inventive method can be carried out in the image reconstruction device.

In accordance with an embodiment of the invention the image reconstruction device also has a material decomposition unit for computing a material decomposition on the basis of the reconstructed result image data. Advantageously the result image data can be further processed directly in the image reconstruction device.

An embodiment of the invention further relates to a computed tomography system, which has a projection data recording unit, comprising an x-ray source and a detector apparatus for recording of projection measurement data of an examination region of an object to be examined, a control device for activating the projection data recording unit and an image reconstruction device. Advantageously, in an embodiment, the computed tomography system is configured for carrying out an embodiment of the method.

An embodiment of the invention further relates to a computer program product with a computer program, which is able to be loaded directly into a memory device of a computed tomography system, with program sections for carrying out all steps of an embodiment of the inventive method when the computer program is executed in the control device of the computed tomography system. Advantageously, in an embodiment, the computer program product can be used so that a computed tomography system can carry out an embodiment of the inventive method.

An embodiment of the invention further relates to a computer-readable medium, on which program sections able to be read in and executed by a computing unit are stored, in order to execute all steps of an embodiment of the inventive method when the program sections are executed by the processing unit. Advantageously, in an embodiment, the computer-readable medium can be used so that a computed tomography system can carry out an embodiment of the inventive method.

Figure 1:
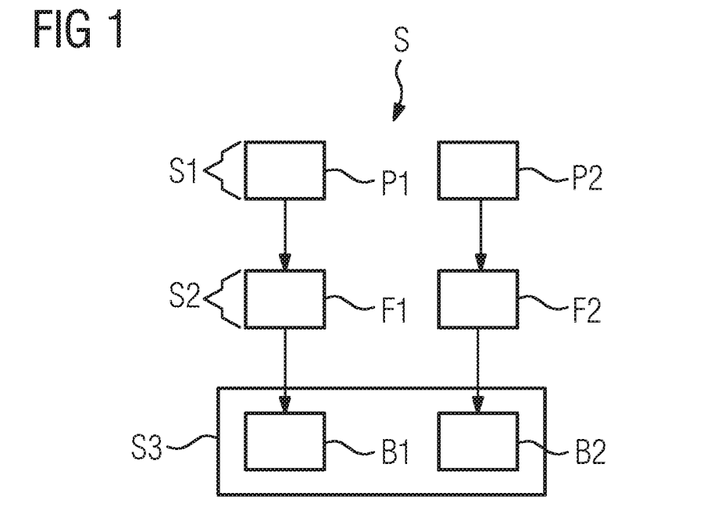
FIG. 1 shows a schematic diagram of a concept of an inventive method in accordance with a first form of embodiment.

FIG. 1 shows a typical version of an embodiment of the inventive method S for imaging of an examination region of an object to be examined with a computed tomography system in accordance with a first form of embodiment. The method S has the steps of the recording S1, the creation S2 of first start image data F1 and second start image data F2 and the coupled iterative reconstruction S3. In the step of recording S1, first projection measurement data P1 and second projection measurement data P2 different from the first projection measurement data P1 are recorded with a common x-ray source-detector system, wherein the first projection measurement data P1 is recorded with a first x-ray spectrum in a first angular sector of maximum 180° and the second projection measurement data P2 is recorded with a second x-ray spectrum different from the first x-ray spectrum in a second angular sector of maximum 180° disjoint from the first angular sector. The first angular sector and the second angular sector comprise an angular area of far less than 180°. The first angular sector and the second angular sector can comprise an angular area of 60° to 180°, preferably of 70° to 140° and especially preferably of 80° to 120°. The first angular sector and the second angular sector can comprise different angular areas. In the step of creation S2, first start image data F1 is created from the first projection measurement data P1 and second start image data F2 from the second projection measurement data P2 via filtered back projection. In the step of coupled iterative reconstruction S3, first result image data B1 is reconstructed on the basis of the first start image data F1 and second result image data B2 on the basis of the second start image data F2, wherein the first result image data B1 and the second result image data B2 feature a complete image of the examination region.

The first projection measurement data P1 and the second projection measurement data P2 is recorded in a single scan with a common x-ray source-detector system in the recording step S1, i.e. for example during an advancing movement in a single direction and during an orbit. The first projection measurement data P1 and the second projection measurement data P2 comprises pre-processed raw data, which for example already takes account of detector-related or geometrical differences between the registered intensities. The first projection measurement data P1 can be pre-processed differently from the second projection measurement data P2.

The first start image data F1 and second start image data F2 are entered as vectors $\vec{X^1}, \vec{X^2}$ into a spatial-spectral image matrix X, wherein the start image data for the different x-ray spectra is entered into the columns of the image matrix.

$$X = (\vec{X^1}, \vec{X^2}) = \begin{pmatrix} X_1^1 & X_1^2 \\ \vdots & \vdots \\ X_M^1 & X_M^2 \end{pmatrix} \quad (9)$$

The image matrix is an M×2 matrix, wherein the image vectors each have M entries and the number of x-ray spectra amounts to 2 here by way of example. The vectors of the first start image data F1 and second start image data F2, recorded with different x-ray spectra, can be arranged in the image matrix, wherein the entries of the image voxels are arranged in one dimension and the spectral information is arranged in the other dimension. The matrix can also be written as a column vector $\vec{X}$ with 2M rows.

The coupled iterative reconstruction S3, by simultaneously taking account of the first start image data F1 and the second start image data F2, can advantageously create complete first result image data B1 and second result image data B2. The coupling or the taking into account of the first start image data F1 and the second start image data F2 in the coupled iterative reconstruction S3 is illustrated in FIG. 1 by the box.

Figure 2:
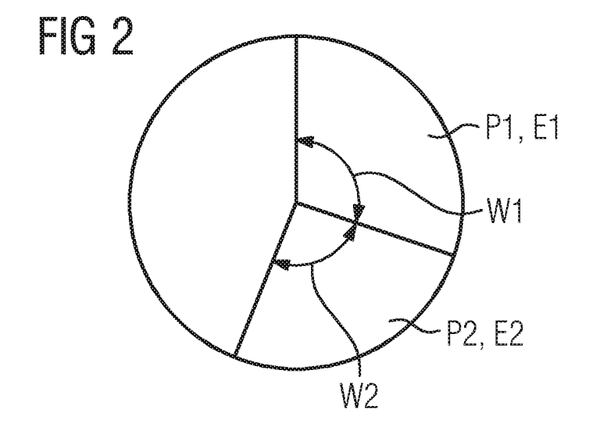
FIG. 2 shows a schematic diagram of a concept of recording in a first angular sector and in a second angular sector in accordance with a first form of embodiment of the inventive method.

FIG. 2 shows a typical version of an embodiment of the inventive recording S1 in a first angular sector W1 and in a second angular sector W2 in accordance with a first form of embodiment of the inventive method S. The first angular sector W1 and the second angular sector W2 typically each comprise an angular area of around 80°. In the first angular sector W1 first projection measurement data P1 is recorded with a first x-ray spectrum E1. In the second angular sector W2 second projection measurement data P2 is recorded with a second x-ray spectrum E2. The first angular sector W1 and the second angular sector W2 are disjoint and are adjacent to each other.

Figure 3:
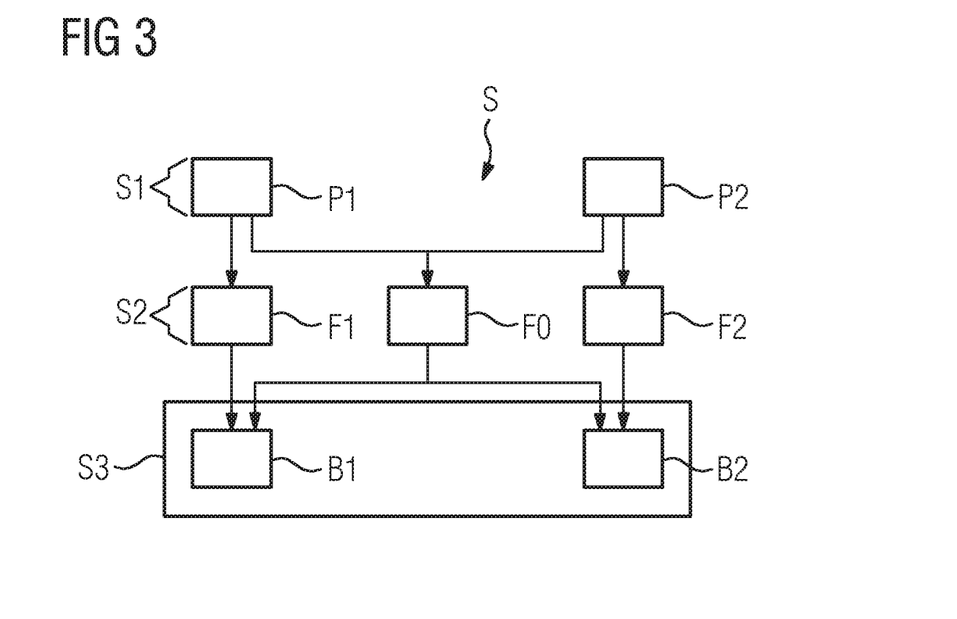
FIG. 3 shows a schematic diagram of a concept of an inventive method in accordance with a second form of embodiment.

FIG. 3 shows a typical version of the inventive method S in accordance with a second form of embodiment. In the coupled iterative reconstruction S3 complete start image data F0 of a complete start image from a common reconstruction based on a number of projection measurement data P1, P2 of a recording S1 is taken into account. The complete start image data F0 is determined via filtered back projection from the first projection measurement data P1 and the second projection measurement data P2.

The complete start image data F0 can be entered as vector $\vec{X^0}$ into a column of the image matrix.

$$X_p = \left(\overrightarrow{X^0} \mid X\right) = \left(\overrightarrow{X^0}, \overrightarrow{X^1}, \overrightarrow{X^2}\right) = \begin{pmatrix} X_1^0 & X_1^1 & X_1^2 \\ \vdots & \vdots & \vdots \\ X_M^0 & X_M^1 & X_M^2 \end{pmatrix} \quad (10)$$

The image matrix $X_p$ can accordingly be an M×(N+1) matrix, all further method steps can be carried out similarly to the use of the M×N matrix. The complete start image data F0 preferably comprises projection measurement data P1, P2 of more than 180° in total, in particular of at least the sum of 180° and the fan angle.

Figure 4:
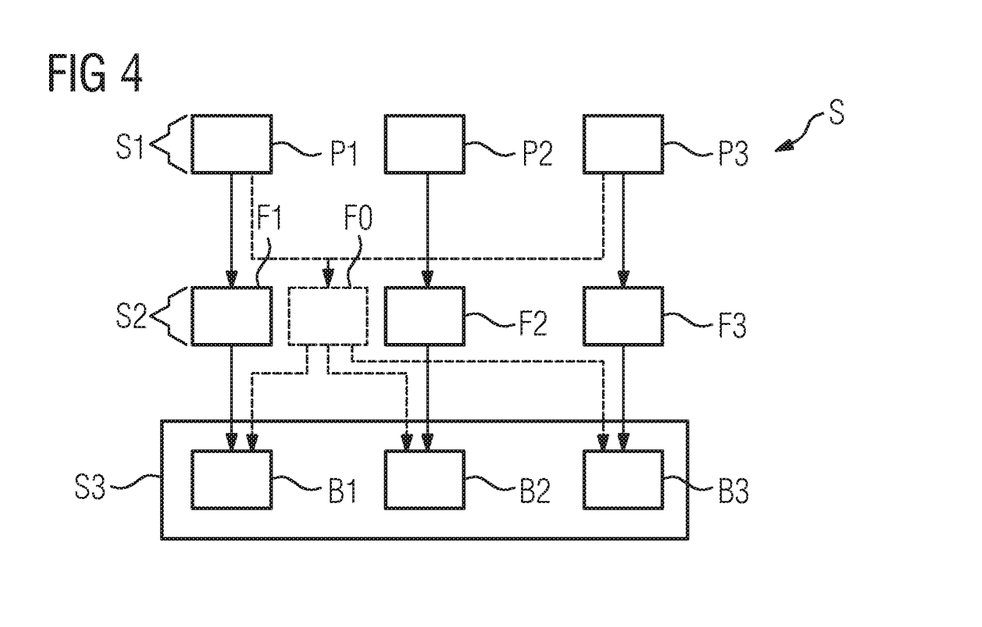
FIG. 4 shows a schematic diagram of a concept of an inventive method in accordance with a third form of embodiment.

FIG. 4 shows a typical version of an embodiment of the inventive method S in accordance with a third form of embodiment. In the recording step S1 third projection measurement data P3 with a third x-ray spectrum different from the first x-ray spectrum and from the second x-ray spectrum is recorded in a third angular sector of maximum 180° disjoint from the first angular sector and from the second angular sector. The image matrix X is $$X = \left(\overrightarrow{X^1}, \overrightarrow{X^2}, \overrightarrow{X^3}\right) = \begin{pmatrix} X_1^1 & X_1^2 & X_1^3 \\ \vdots & \vdots & \vdots \\ X_M^1 & X_M^2 & X_M^3 \end{pmatrix} \quad (11)$$

or the image matrix $X_p = (\overrightarrow{X^0} \mid X)$ is $$X_p = \left(\overrightarrow{X^0} \mid X\right) = \left(\overrightarrow{X^0}, \overrightarrow{X^1}, \ldots, \overrightarrow{X^3}\right) = \begin{pmatrix} X_1^0 & X_1^1 & X_1^2 & X_1^3 \\ \vdots & \vdots & \vdots & \vdots \\ X_M^0 & X_M^1 & X_M^2 & X_M^3 \end{pmatrix}. \quad (12)$$

Figure 5:
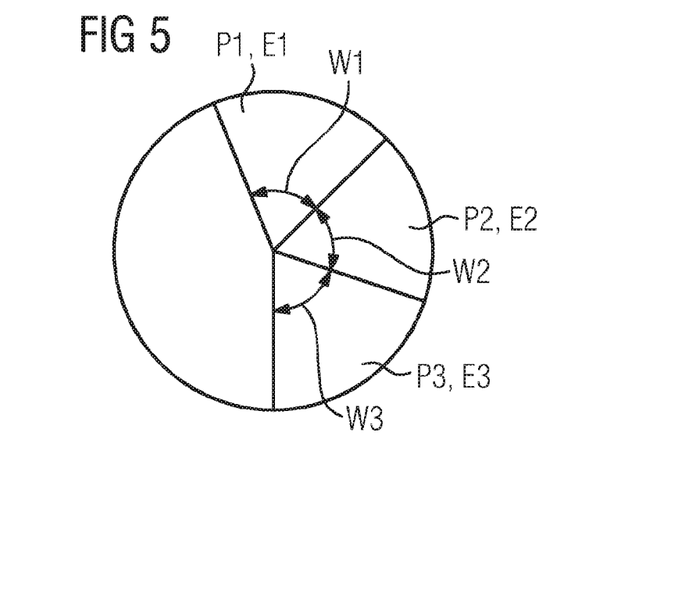
FIG. 5 shows a schematic diagram of a concept of recording in a first angular sector, in a second angular sector and in a third angular sector in accordance with a third form of embodiment of the inventive method.

FIG. 5 shows a typical way of carrying out an embodiment of the inventive recording in a first angular sector W1, a second angular sector W2 and a third angular sector W3 in accordance with a third form of embodiment of the inventive method. In the third angular sector W3 third projection measurement data P3 is recorded with a third x-ray spectrum E3. The first angular sector W1, the second angular sector W2 and the third angular sector W3 are disjoint and adjoin one another.

Figure 6:
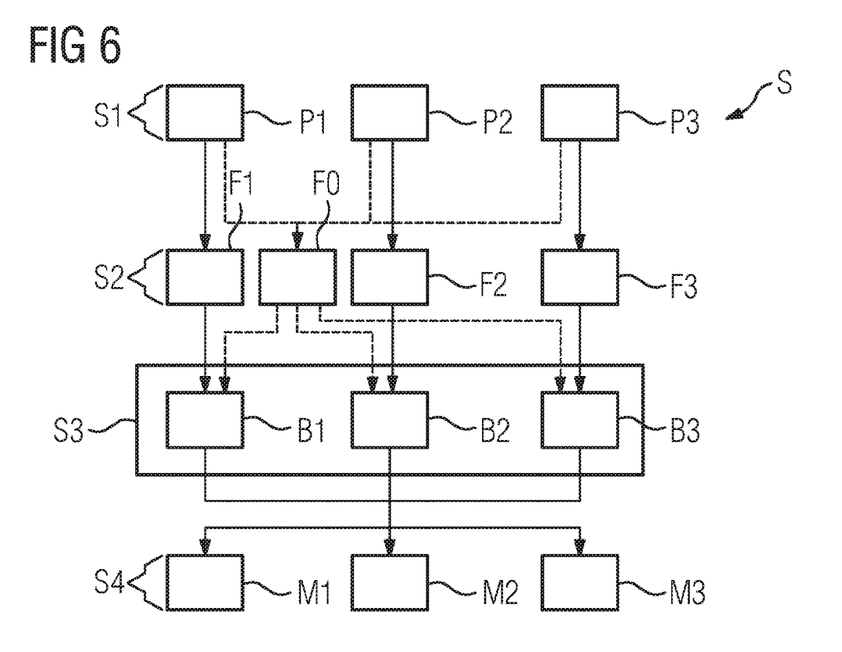
FIG. 6 shows a schematic diagram of a concept of an inventive method in accordance with a fourth form of embodiment.

FIG. 6 shows a typical way of carrying out an embodiment of the inventive method S in accordance with a fourth form of embodiment. The method S further has the step of a material decomposition S4 on the basis of the result image data B1, B2, B3. The first result image data B1, second result image data B2 and third result image data B3 can be represented as a pixel-by-pixel linear combination and a material decomposition into three basic materials can be achieved thereby. The material decomposition makes possible the presentation of material images based on one basic material in each case. For example gadolinium, iodine, calcium or water can be used as the basic material. Similarly, with the inventive method S, the material decomposition S3 into two basic materials can be undertaken on the basis of the first projection measurement data P1 and the second projection measurement data P2 (not shown).

Figure 7:
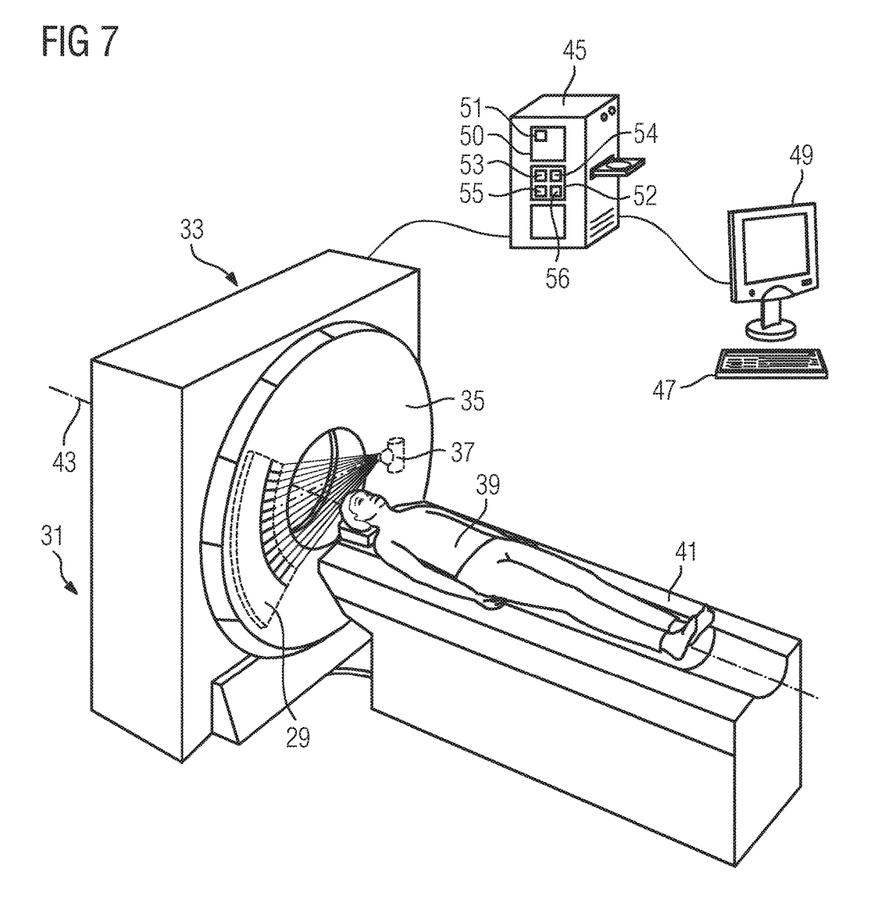
FIG. 7 shows a schematic diagram of a concept of an inventive computed tomograph.

FIG. 7 shows a typical form of embodiment of the inventive computed tomography system 31 for carrying out an embodiment of the inventive method. The computed tomography system 31 contains a projection data recording unit 33 with a rotor 35. The rotor 35 comprises an x-ray source 37 and the detector apparatus 29. The object 39 is supported on the patient couch 41 and is able to be moved along the axis of rotation z 43 through the projection data recording unit 33. For control and computing of the slice images a computer unit 45 is used. The computer unit 45 comprises a control device 50 with a memory device 51. The computer unit 45 further comprises an image reconstruction device 52 with an input interface 53, a reconstruction unit 54, an image data interface 55 and a material decomposition unit 56. An input device 47 and an output apparatus 49 are connected to the computer unit 45.

Although the invention has been illustrated and described in greater detail by the preferred example embodiment, the invention is not restricted by the disclosed examples and other variations can be derived herefrom by the person skilled in the art, without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing a complete image of an examination region of an object to be examined using a computed tomography system, the method comprising:
    recording first projection measurement data and second projection measurement data, different from the first projection measurement data, with a common x-ray source-detector system, the first projection measurement data being recorded with a first x-ray spectrum in a first angular sector of maximum 180° and the second projection measurement data being recorded with a second x-ray spectrum, different from the first x-ray spectrum, in a second angular sector of maximum 180° disjoint from the first angular sector;

creating first start image data from the first projection measurement data and creating second start image data from the second projection measurement data via a first reconstruction method; and performing coupled iterative reconstruction of first result image data based on the first start image data and performing coupled iterative reconstruction of second result image data based on the second start image data, the first result image data and the second result image data each including a complete image of the examination region.

2. The method of claim 1, wherein complete start image data of a complete start image from a common reconstruction from a number of items of projection measurement data of a recording is taken into account in the coupled iterative reconstruction.

3. The method of claim 2, wherein in addition third projection measurement data with a third x-ray spectrum, different from the first x-ray spectrum and from the second x-ray spectrum, is recorded in a third angular sector of maximum 180°, disjoint from the first angular sector and disjoint from the second angular sector.

4. The method of claim 2, wherein the coupled iterative reconstruction comprises a minimization with a regularization.

5. The method of claim 2, further comprising: performing material decomposition based upon the result image data.

6. The method of claim 2, wherein an average photon energy or an maximum photon energy of the different first and second x-ray spectra is different by at least 10 keV.

7. The method of claim 1, wherein in addition third projection measurement data with a third x-ray spectrum, different from the first x-ray spectrum and from the second x-ray spectrum, is recorded in a third angular sector of maximum 180°, disjoint from the first angular sector and disjoint from the second angular sector.

8. The method of claim 7, wherein an average photon energy or an maximum photon energy of the different first, second and third x-ray spectra is different by at least 10 keV.

9. The method of claim 7, wherein a switchover between the different first, second and third x-ray spectra comprises a use of a filter in the beam path of the x-ray source or a change of tube voltage of the x-ray source.

10. A non-transitory computer program product including a computer program, directly loadable into a memory device of a control device of a computed tomography system, including program sections for carrying out the method of claim 7, when the computer program is executed in the control device of the computed tomography system.

11. A non-transitory computer-readable medium, on which program sections able to be read in and executable by a computer unit are stored, to carrying out the method of claim 7, when the program sections are executed by the computer unit.

12. The method of claim 1, wherein the coupled iterative reconstruction comprises a minimization with a regularization.

13. The method of claim 1, further comprising: performing material decomposition based upon the result image data.

14. The method of claim 1, wherein an average photon energy or an maximum photon energy of the different first and second x-ray spectra is different by at least 10 keV.

15. The method of claim 1, wherein a switchover between the different first and second x-ray spectra comprises a use of a filter in the beam path of the x-ray source or a change of tube voltage of the x-ray source.

16. A non-transitory computer program product including a computer program, directly loadable into a memory device of a control device of a computed tomography system, including program sections for carrying out the method of claim 1, when the computer program is executed in the control device of the computed tomography system.

17. A non-transitory computer-readable medium, on which program sections able to be read in and executable by a computer unit are stored, to carrying out the method of claim 1, when the program sections are executed by the computer unit.

18. An image reconstruction device, comprising:
an interface to receive first projection measurement data and second projection measurement data, different from the first projection measurement data, obtained via a computed tomography system with the aid of a recording from an examination region of an object to be examined, the first projection measurement data being recorded with a first x-ray spectrum in a first angular sector of maximum 180° and the second projection measurement data being recorded with a second x-ray spectrum, different from the first x-ray spectrum, in a second angular sector of maximum 180° disjoint from the first angular sector;
a memory to store the acquired projection measurement data and to store computer executable instructions;
a processor configured to execute the computer executable instructions to
create first start image data from the first projection measurement data and create second start image data from the second projection measurement data via a first reconstruction method, and
perform coupled iterative reconstruction of first result image data based on the first start image data and perform coupled iterative reconstruction of second result image data based on the second start image data, the first result image data and the second result image data each including a complete image of the examination region; and
a display to output a reconstructed result image data of the first result image data and the second result image data based upon the preformed iterative reconstruction.

19. The image reconstruction device of claim 18, wherein the processor is further configured to execute the computer readable instructions to compute a material decomposition based upon the reconstructed result image data.

20. A computed tomography system, comprising:
an x-ray source and a detector apparatus to record projection measurement data of an examination region of an object to be examined,
a controller to activate the projection data recording unit, and
the image reconstruction device of claim 19.

21. A computed tomography system, comprising:
an x-ray source and a detector apparatus to record projection measurement data of the examination region of the object to be examined,
a controller to activate the projection data recording unit, and
the image reconstruction device of claim 18.

22. A device for producing a complete image of an examination region of an object to be examined using a computed tomography system, the method comprising:
means for recording first projection measurement data and second projection measurement data, different from the first projection measurement data, the first projection measurement data being recorded with a first x-ray spectrum in a first angular sector of maximum 180° and the second projection measurement data being recorded with a second x-ray spectrum, different from the first x-ray spectrum, in a second angular sector of maximum 180° disjoint from the first angular sector;

means for creating first start image data from the first projection measurement data and for creating second start image data from the second projection measurement data via a first reconstruction method; and means for performing coupled iterative reconstruction of first result image data based on the first start image data and performing coupled iterative reconstruction of second result image data based on the second start image data, the first result image data and the second result image data each including a complete image of the examination region.

23. The device of claim 22, wherein complete start image data of a complete start image from a common reconstruction from a number of items of projection measurement data of a recording is taken into account in the coupled iterative reconstruction.

24. The device of claim 22, wherein in addition third projection measurement data with a third x-ray spectrum, different from the first x-ray spectrum and from the second x-ray spectrum, is recorded in a third angular sector of maximum 180°, disjoint from the first angular sector and disjoint from the second angular sector.

25. The device of claim 22, wherein the coupled iterative reconstruction comprises a minimization with a regularization.

26. The device of claim 22, further comprising:

means for performing material decomposition based upon the result image data.

27. The device of claim 22, wherein an average photon energy or an maximum photon energy of the different first and second x-ray spectra is different by at least 10 keV.

28. The device of claim 22, wherein a switchover between the different first and second x-ray spectra comprises a use of a filter in the beam path of an x-ray source or a change of tube voltage of an x-ray source.

* * * * *